US008603460B2

(12) United States Patent
Connolly

(10) Patent No.: US 8,603,460 B2
(45) Date of Patent: Dec. 10, 2013

(54) **METHOD OF MAKING A *LACTOBACILLUS REUTERI* WITH INCREASED ACID TOLERANCE**

(75) Inventor: Eamonn Connolly, Lidingö (SE)

(73) Assignee: Brogaia AB, Lerum (SE)

( * ) Notice: Subject to any disclaimer, the term of this patent is extended or adjusted under 35 U.S.C. 154(b) by 1948 days.

(21) Appl. No.: 11/446,648

(22) Filed: Jun. 5, 2006

(65) Prior Publication Data
US 2007/0280914 A1    Dec. 6, 2007

(51) Int. Cl.
*A01N 63/00*    (2006.01)
(52) U.S. Cl.
USPC .................. 424/93.45; 435/252.9; 435/440
(58) Field of Classification Search
None
See application file for complete search history.

(56) References Cited

U.S. PATENT DOCUMENTS

| 4,518,696 | A | 5/1985 | Gehrman et al. |
| 5,439,678 | A | 8/1995 | Dobrogosz et al. |
| 5,458,875 | A | 10/1995 | Casas-Perez et al. |
| 5,534,253 | A | 7/1996 | Casas et al. |
| 5,800,813 | A | 9/1998 | Casas |
| 5,837,238 | A | 11/1998 | Casas et al. |
| 5,849,289 | A | 12/1998 | Dobrogosz et al. |
| 6,036,952 | A | 3/2000 | Oh |
| 6,100,388 | A | 8/2000 | Casas et al. |
| 6,103,227 | A | 8/2000 | Wolf et al. |
| 2004/0067573 | A1 | 4/2004 | Connolly et al. |
| 2004/0208863 | A1 | 10/2004 | Versalovic et al. |

OTHER PUBLICATIONS

Chin et al., J. Microbiol., vol. 43, pp. 251-256 (2005).*
Vescovo et al., Applied and Environmental Microbiology, vol. 43, pp. 50-56 (1982)).*
Vescovo et al., FEMS Microbiology Letters, vol. 23, Issue 2-3 , pp. 333-334).*
Reid et al., World J Urol (2006) 24: 28-32.*
Axelsson et al., Plasmid,vol. 20, Issue 2, Sep. 1988, pp. 171-174.*
G. Rollan et al. / Food Microbiology 20 (2003) 313-319.*
Taranto et al., 2000 J Dairy Sci 83:401-403.*

* cited by examiner

*Primary Examiner* — Irene Marx
(74) *Attorney, Agent, or Firm* — Lynn E. Barber

(57) ABSTRACT

The invention provides certain plasmid cured strains of lactic acid bacteria modified for their capability of better acid-tolerance, a method of modifying such strains, and products containing such strains.

1 Claim, 2 Drawing Sheets

METHOD OF MAKING A *LACTOBACILLUS REUTERI* WITH INCREASED ACID TOLERANCE

FIELD OF THE INVENTION

Background of the Invention

In 1908, the Russian biologist Eli Metchnikoff credited the long lives of certain Bulgarian and Russian citizens to the consumption of large amounts of fermented milk products. The key organism in these foods was later identified as *Lactobacillus acidophilus*, a lactic acid-producing bacteria. The lactic acid-producing bacteria are so named for their ability to produce lactate. However, lactate production is only one of many benefits derived from this collection of bacteria.

Based on the work of Metchnikoff and others, scientists developed the idea of probiotic microorganisms, directly feeding live, lactic acid-producing bacteria and yeast to animals for improving their health and performance. The observed benefits may result from: 1) competition for attachment sites in the digestive tract, 2) competition for essential nutrients, 3) production of anti-microbial substances, 4) increasing the growth of beneficial bacteria and 5) stimulating the immune system.

Some disease-causing bacteria reduce an animal's ability to absorb nutrients by disrupting the lining of the small intestine. Studies indicate that the lactic acid-producing bacteria attach to the small intestine and produce substances to prevent disease-causing organisms from binding to the intestinal wall. In addition, the attachment of the beneficial bacteria may increase the absorptive surface area of the small intestine and enhance enzyme activity for greater nutrient absorption by the animal.

Bacteria, both health-promoting and disease-causing, require certain nutrients for growth. Lactic acid-producing bacteria could utilize vitamins, amino acids or other nutrients that might otherwise support the growth of harmful bacteria.

Considerable research has focused on the ability of direct-fed microbial cultures to produce substances that inhibit disease-causing organisms. Lactic, acetic and formic acid lower the intestinal pH to create an environment unsuitable for harmful organisms. Lactic acid-producing bacteria also secrete hydrogen peroxide, resulting in conditions unfavorable for oxygen-requiring microorganisms.

Two groups of antimicrobial substances have been identified, low molecular weight antimicrobial substances, for example, reuterin, produced by *L. reuteri*; and bacteriocins. Bacteriocins are microbial-produced substances that inhibit the growth of bacteria which are often genetically related. Bacteriocins are polypeptides and their inhibitory properties are destroyed by proteases while reuterin, a broad-spectrum antimicrobial substance, is not a polypeptide and its antimicrobial activity is unaffected by proteases.

Strains of a wide variety of *Lactobacillus* species, including *L. reuteri* have been used in probiotic formulations. *Lactobacillus reuteri* is one of the naturally occurring inhabitants of the gastrointestinal tract of animals, and is routinely found in the intestines of healthy animals, including humans. It is known to have antimicrobial activity. See, for example U.S. Pat. Nos. 5,439,678, 5,458,875, 5,534,253, 5,837,238, and 5,849,289. When *L. reuteri* cells are grown under anaerobic conditions in the presence of glycerol, they produce the antimicrobial substance known as β-hydroxy-propionaldehyde (3-HPA).

Research has documented the ability of lactic acid-producing bacteria to inhibit *E. coli, Salmonella typhimurium, Staphylococcus aureus* and *Clostridium perfringens*. The reduction of diarrhea-causing organisms is especially important in newborn and young animals.

Genetic modifications to *Lactobacillus* strains are normally targeted toward the improvement or augmentation of specific strain characteristics, such as the production of compounds antagonistic to common food pathogens, the ability to metabolize cholesterol or to tolerate acid or bile, and immune response-enhancing abilities (Kullen, M. J. and T. R. Klaenhammer. 1999. Genetic modification of intestinal lactobacilli and bifidobacteria, p. 65-83. In G. Tannock (ed.), Probiotics: A Critical Review, Horizon Scientific Press, Wymondham, U.K.). Under ideal conditions, these modified strains would benefit the host. However, under natural conditions, the performance of the modified *Lactobacillus* strains is frequently affected by indigenous plasmids, especially in cases in which the manipulations are plasmid-mediated. Incompatibility between the indigenous plasmids and the introduced plasmids is one of the principal factors contributing to plasmid instability within a host (Posno, M., R. J. Leer, N. van Luijk, M. J. f. van Giezen, P. T. H. M. B. C. Lokman, and P. H. Pouwels. 1991. Incompatibility of Lactobacillus vectors with replicons derived from small cryptic Lactobacillus plasmids and segregational instability of the introduced vectors. Appl. Environ. Microbiol. 57, 1822-1828).

Most *Lactobacillus* strains, regardless of their source (plants, meat, silage, sourdough or gastrointestinal tract), harbor at least one indigenous plasmid, and often more (Pouwels, P. H. and R. J. Leer. 1993. Genetics of lactobacilli: Plasmids and gene expression. Antonie van Leeuwenhoek 64, 85-107). These plasmids may not only interfere with the stability of the recombinant plasmid, but may also harbor undesirable traits, e.g. antibiotic resistance (Posno et al., 1991) and it may become advantageous or even necessary to eliminate any such indigenous plasmids.

Many antibiotics and antimicrobial substances have naturally been present in nature for millions of years and man has used antibiotics and antimicrobials to inhibit the growth of bacteria or other microbes and to treat bacterial or microbial infections in humans, other animals, and in tissue culture. The use of antibiotics or antimicrobials, however, has the undesirable effect of selecting for bacteria or other microbes which are resistant to those antibiotics or antimicrobials which are administered or applied. As a result, treatment regimens can be adversely affected or, in some cases, rendered ineffective.

*L. reuteri* ATCC 55730, has recently been reported to be resistant towards lincomycin and also to contain the resistance gene lnuA (Kastner, S., Perreten, V., Bleuler, H., Hugenschmidt, G., Lacroix, C. & Meile, L. 2006. Antibiotic susceptibility patterns and resistance genes of starter cultures and probiotic bacteria used in food. Syst Appl Microbiol. 29(2): 145-155). The genome of the strain was searched for this gene and it was identified as the open reading frame 1r2105 on plasmid pLR585. The plasmid also harbors genes encoding a multidrug resistance protein (1r2089) and a polyketide antibiotics exporter (1r2096 and 1r2097). None of the genes on the plasmid have any obvious connection or relevance of importance for the known probiotic characteristics or acid tolerance of the strain.

There is a need, especially in the probiotic industry, to use lactobacilli that tolerate acids well in order for such cultures in various formulations not only to pass through the acid environment of the stomach to reach the remainder of the gut in sufficient numbers, but also to be able to grow and colonize the stomach, to be able to exert their probiotic effect throughout the gastrointestinal tract. When strains that tolerate acid poorly are used, higher numbers of bacteria need to be ingested which leads to higher cost. Further, much effort is directed towards protecting the cultures from acid pH by various means, which also increases cost. There is, therefore, an interest in the industry to have strains that tolerate acids well, and consequently in methods that will improve the acid tolerance of existing strains. One example of a method of improving the acid tolerance of lactic acid bacteria is given in patent-application US20050158423 A1, where strains carrying plasmids encoding for small heat shock proteins are used, and also methods for transferring such plasmids into a lactic acid bacteria are given. This is however in contrast to the present invention where a plasmid is removed to increase the acid tolerance of the strain.

Other objects and features of the inventions will be more fully apparent from the following disclosure and appended claims.

SUMMARY OF THE INVENTION

Figure 1:
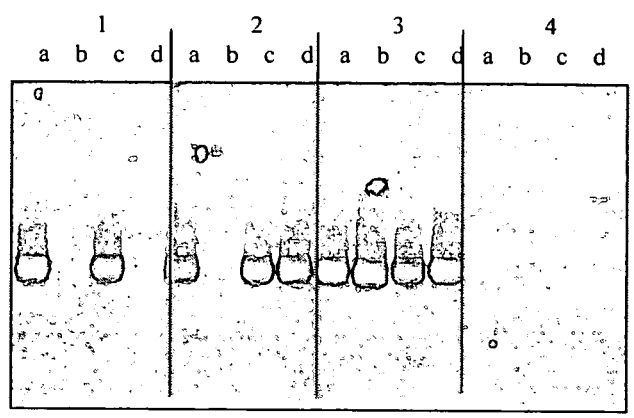
FIG. 1. Shows the detection of plasmids with PCR. The numbers represent: 1, L. reuteri DSM 17938; 2, L. reuteri DSM 17686; 3, L. reuteri ATCC 55730; and 4, L. reuteri DSM 20016 (negative control). The analyzed plasmids are: a, pLR580; b, pLR581; c, pLR584; and d, pLR585.

A strain derived from L. reuteri ATCC 55730 by curing the two plasmids pLR581 and pLR585 has been obtained. This strain is much more sensitive to tetracycline and lincomycin than the parental strain. The double cured strain has been deposited at DSMZ and has been designated L. reuteri DSM 17938. L. reuteri DSM 17938 has the same rep-PCR (repetitive PCR) profile, fermentation pattern, reuterin production, morphology, growth rate, adhesion to mucus and bile tolerance as L. reuteri ATCC 55730. However, the cured strain grows to a higher density and survives better in acidic conditions. When the strains are co-cultured DSM 17938 is also more competitive.

Thus the invention herein makes use of the characteristics of the new strain and provides certain plasmid cured strains of lactic acid bacteria modified such that they display better acid tolerance, a method of modifying such strains, and products containing such strains. Other objects and features of the inventions will be more fully apparent from the following disclosure and appended claims.

DETAILED DESCRIPTION OF THE INVENTION AND PREFERRED EMBODIMENTS THEREOF

The L. reuteri strain DSM 17938 (deposited at DSMZ-Deutsche Sammlung von Mikroorganismen und Zellkulturen GmbH (Mascheroder Weg 1b, D-38124 Braunschweig) on Feb. 6, 2006, under the Budapest Treaty) is derived from L. reuteri ATCC 55730 by curing the two plasmids pLR581 and pLR585. It has the same rep-PCR profile, fermentation pattern, reuterin production, morphology, growth rate, adhesion to mucus and bile tolerance as ATCC 55730 but is much more sensitive to tetracycline and lincomycin than the parental strain. Surprisingly, L. reuteri DSM 17938 and DSM 17686 are found to bring about an increase in acid tolerance due to a plasmid removal through curing. It is more competitive in the co-culture experiments, which can be explained by a better survival at acidic pH.

One object of this invention is to remove a plasmid from a lactic acid bacteria to make it tolerate acids better and thereby survive better in the gut and consequently be more beneficial to human health. This has been shown in L. reuteri strain DSM 17686 and in the new strain L. reuteri strain DSM 17938. This seems to be a general and previously unknown phenomena in lactobacilli that a removed plasmid, without coding for anything related to acid tolerance, will give a new strain which is more stable to acids. This effect has been used in the invention herein to make lactobacilli more acid tolerant.

Other objects and features of the invention will be more fully apparent from the following disclosure and appended claims.

Example 1

Curing of pLR585 From DSM 17686

Plasmid curing by protoplast formation and regeneration was conducted essentially as described in Vescovo et al. (Vescovo, M., Morelli, L., Cocconcelli, P. S., and Bottazzi, V. 1984. Protoplast formation, regeneration and plasmid curing in Lactobacillus reuteri. FEMS Microbiol Lett 23:333-334). An overnight culture of Lactobacillus reuteri DSM 17686 was diluted to OD600=0.1 in a 10 ml MRS culture (Oxoid, Lenexa, Kans., USA) and grown at 37° C. until OD600=0.7-0.8. Cells were collected by centrifugation at 3000×g for 10 minutes and washed in 10 ml Nanopure water. Cells were collected again by centrifugation and re-suspended in 2 ml of protoplast buffer (0.2 M phosphate buffer, 0.5 M sucrose, 20 mM $MgCl_2$; pH 7.0). The cells were mixed with an equal volume of 10 mg $ml^{-1}$ lysozyme in protoplast buffer and incubated at 37° C. for 1 h. Protoplasts were harvested by centrifugation at 3000×g for 15 minutes and washed with 20 ml protoplast buffer. Protoplasts were harvested again by centrifugation and re-suspended in 1 ml of protoplast buffer after which a microscopic observation was performed.

Dilutions in protoplast buffer were plated on MRS agar with 0.5 M sucrose for regeneration. Dilutions in Nanopure water were plated on MRS agar to assess the number of remaining whole cells. The number of cfu's was determined after an overnight anaerobic incubation at 37° C. and again after one further overnight incubation. Regenerated colonies were picked to MRS agar with and without 8 μg $ml^{-1}$ lincomycin. Plasmid cured candidates were identified by non-growth on MRS plates with lincomycin.

Result:
Confirmation of the Curing of pLR585

Figure 2:
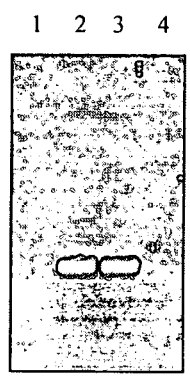
FIG. 2. Shows the detection of the resistance gene lnuA. 1, DSM 17938; 2, DSM 17686; 3, ATCC 55730; 4, DSM 20016

The plasmids of DSM 17938 were analyzed with PCR (FIG. 1). Both pLR585 and pLR581 were absent, whereas the other two plasmids were still found. Thus, DSM 17938 is cured from both the tetW-plasmid pLR581 and the lnuA-plasmid pLR585. The absence of lnuA in DSM 17938 was also detected by PCR (FIG. 2).

Example 2

Determination of Minimal Inhibitory Concentrations of Lincomycin

The bacteria were grown in MRS broth for 16 h at 37° C. After dilution to $10^5$ cfu $ml^{-1}$, 1 μl of each bacterial strain was spotted on MRS plates containing lincomycin or clindamycin (concentrations 0, 0.125, 0.25, 0.5, 1, 2, 4, 8 and 16 μg $ml^{-1}$). After adsorption of the drops, the plates were incubated in anaerobic atmosphere at 37° C. for 24 h. The MIC was defined as the lowest antibiotic concentration for which there was no visible bacterial growth. MICs to tetracycline were tested with Etest (AB Biodisk) on bacteria growing on MRS agar (Oxoid) plates according to the instructions from the manufacturer.

Result:

The curing of pLR585 resulted in a decrease of MIC from >16 to 0.25 μg ml$^{-1}$ lincomycin, close to the level of the negative control DSM 20016. The already very low MIC value for clindamycin was not changed. Also the MICs to tetracycline were tested with E-test and found to be 12-16 μml-1 for DSM 17938 and DSM 17686 and >256 μg ml$^{-1}$ for ATCC 55730.

TABLE 1

| Strain | DSM 17938 | DSM 17686 | ATCC 55730 | DSM 20016 | 1063 |
|---|---|---|---|---|---|
| MIC lincomycin (μg ml$^{-1}$) | 0.5 | >16 | >16 | 0.25 | >16 |
| MIC clindamycin (μg ml$^{-1}$) | <0.125 | <0.125 | <0.125 | <0.125 | >16 |

Example 3

Fermentation Pattern and Reuterin Production

Fermentation patterns were determined using api 50 CHL (bio-Mérieux) according to the instructions from the manufacturer. To detect the reuterin production, the bacteria were first grown for 48 h on MRS plates (inoculated as streaks). The plates were then overlayed with 500 mM glycerol agar (1% agar) and incubated at 37° C. for 30 min. Reuterin was detected by addition of 5 ml 2,4-dinitrophenylhydrazine (0.1% in 2 M HCl). After 3 min incubation, the solution was poured of and 5 ml 5 M KOH was added. Red zones around the colonies show that reuterin has been produced.

Result:

The fermentation pattern of DSM 17938 was compared with DSM 17686 and ATCC 55730 using API 50 CHL and no differences could be detected. All strains fermented L-arabinose, ribose, galactose, glucose, maltose, lactose, melibiose, saccharose, raffinose and gluconate and were negative for the rest of the tests. Also the production of reuterin was of the same magnitude for the three strains.

Example 4

Growth and Co-Culture

The growth was detected by inoculation of an overnight culture to OD 0.1 in MRS broth in tubes prewarmed to 37° C. The tubes were incubated at 37° C. and samples for measuring OD600 nm were taken during 8 h. Each bacterium were analyzed in triplicate. Co-culturing of the bacteria was done by mixing equal amounts of overnight cultures of ATCC 5730, DSM 17686 and DSM 17938 in prewarmed MRS broth tubes. The mixture was incubated at 37° C. overnight and then re-inoculated to a new MRS tube. This procedure was repeated three times. At the start and after every culturing samples were analyzed by plating different dilutions of the culture on MRS plates and then picking colonies to three MRS plates; one without antibiotics, one containing 8 μg ml$^{-1}$ lincomycin and one containing 64 μg ml$^{-1}$ tetracycline. Colonies growing only on MRS were considered to be DSM 17938, those growing on MRS with lincomycin were considered to be DSM 17686, and those growing on all three plates were considered to be ATCC 55730.

Result:

The growth of the strains DSM 17938 and DSM 17686 was compared with ATCC 55730. No difference in generation time could be detected, however, both cured strains grew to a significantly higher density than ATCC 55730. The final ODs were: for ATCC 55730, 4.78±0.13; for DSM 17686, 5.89±0.28; and for DSM 17938, 6.00±0.26. The three strains have also been co-cultured in MRS broth for approximately 30 generations (3 re-inoculations). The results clearly show that the cured strains have an advantage when growing in vitro. Equal amounts of the strains were inoculated together, but at the end of the experiment the mixture consisted of 56% DSM 17938, 38% DSM 17686 and only 6% ATCC 55730. The reason to this might be that the cured strains grow to a higher OD or possibly survive better in stationary phase. The loss of two plasmids might also have resulted in a decreased burden (less DNA to replicate) and thereby higher competitive ability.

Example 5

Binding to Mucus

Mucus from pig small intestine was used. Mucus material and BSA were dissolved and diluted in PBS and immobilized in microtiter wells (Greiner) by incubation of 100 μl of solution for 3 h at room temperature with slow rotation. The final concentrations were OD280 0.1 for the mucus material and 100 μg ml$^{-1}$ for BSA. The wells were blocked with 0.2 ml PBS supplemented with 1% Tween 20 for 1 h, and then washed with PBS with 0.05% Tween 20 (PBST). The bacteria were grown in MRS broth for 16 h at 37° C., washed once in PBST and diluted to OD600 0.5 in the same buffer. The wells were thereafter washed with PBST and the degree of binding was examined with an inverted microscope. All bacteria were analyzed in triplicates.

Result:

The mucus binding capacity of the strains DSM 17938 and DSM 17686 was compared with ATCC 55730. No difference in binding could be detected.

Example 6

Acid Tolerance

In order to test the survival at low pH, *L. reuteri* strains ATCC 55730, DSM 17686 and DSM 17938 were grown overnight at 37° C. in MRS. 5 μl of the bacteria were added to 10 ml pre-warmed MRS, and incubated at 37° C. until an OD600 of 1.0 was reached. After addition of 800 μl OD 1.0 culture to 8 ml synthetic stomach juice (8.3 g l$^{-1}$ proteose peptone (Oxoid), 3.5 g l$^{-1}$ glucose, 2.05 g l$^{-1}$ NaCl, 0.6 g l$^{-1}$ KH$_2$PO$_4$, 0.11 g l$^{-1}$ CaCl$_2$, 0.37 g l$^{-1}$ KCl, adjusted to pH 2.0 with HCl), a modification from Cotter et al. lacking enzymes (Cotter, P. D., Gahan, C. G. & Hill, C. 2001. A glutamate decarboxylase system protects *Listeria monocytogenes* in gastric fluid. Mol Microbiol 40: 465-475). The tubes were incubated at 37° C. and samples removed after 1, 20, 50 and 90 minutes. The samples were diluted in PBS and spread on MRS plates, which were incubated anaerobically for 24 hours at 37° C. The experiment was repeated at two occasions and duplicate samples were analyzed each time. The difference between the strains was tested statistically by the Student's t-test.

Result:

The three strains where grown to OD600 1.0 (mid to late exponential phase) and thereafter challenged with acidic pH.

Figure 3:
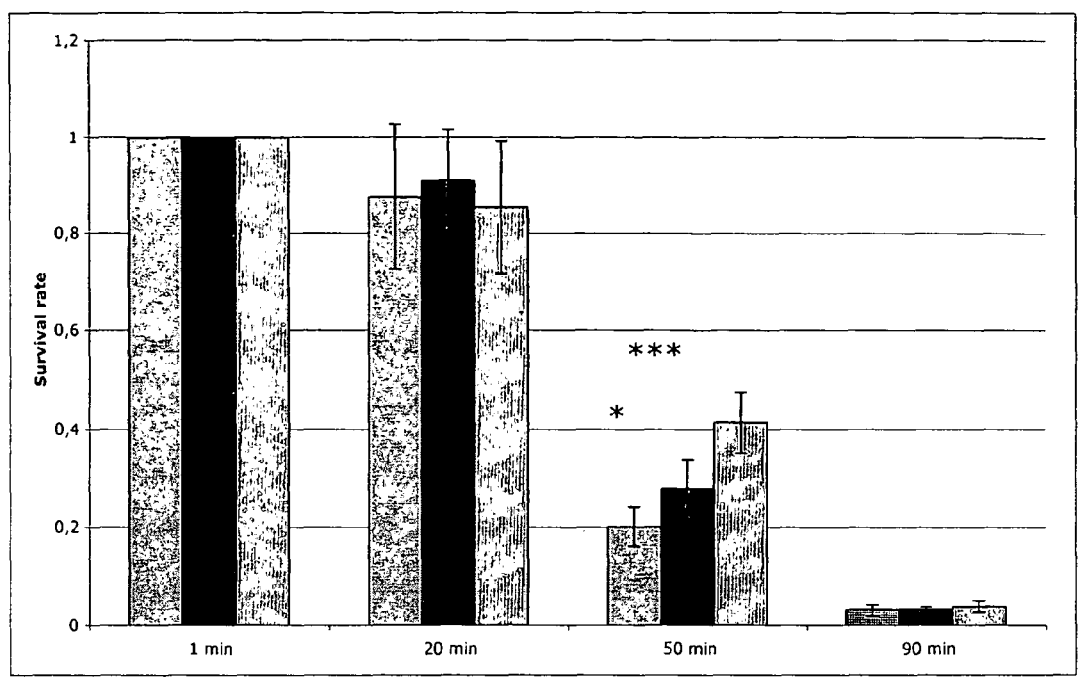
FIG. 3. Acid tolerance of ATCC 55730 (left), DSM 17686 (middle) and DSM 17938 (right) in bars. The columns show the proportion of surviving bacteria (mean of four replicates). The error bars indicates the standard deviation, one star an p-value<0.05 and three stars p<0.001.

Both DSM 17938 and DSM 17686 survived better than ATCC 55730 after 50 min incubation at pH 2.0, with survival rates of 41, 28 and 20%, respectively (FIG. 3). The differences were significant with p-values 0.0006 (DSM 17938 vs. ATCC 55730) and 0.04 (DSM 17686 vs. ATCC 55730). The reason for this is not known. A better survival at acidic pH might be an explanation why the cured strains were more competitive in the co-culture experiments.

Example 7

Bile Tolerance

The bacteria were grown for 16 h in MRS broth at 37° C. The bacterial suspensions were diluted in PBS to approximately $10^3$-$10^6$ cfu ml$^{-1}$. 10 μl of each dilution were dropped onto MRS plates with different concentrations of bovine bile (0, 0.5, 1, 2, 4 and 6%; Sigma B3883). Two replicates of each bacterium were analyzed. The plates were incubated for 72 h at 37° C. in an anaerobic atmosphere. The colonies were counted and the bile tolerance was estimated by comparing the number of colonies on the bile plates with the MRS plate without bile. Bacteria in exponential phase (OD 0.5) were also tested in the same manner.

Result:

The tolerances of the cured strains DSM 17938 and DSM 17686 to bovine bile were compared with ATCC 55730. The bacteria were tested both in stationary and exponential (OD600 0.5) growth phases. They tolerate bile well when they are in stationary phase but the survival and growth were much lower in exponential phase. However, no difference in tolerance could be detected between the strains.

While the invention has been described with reference to specific embodiments, it will be appreciated that numerous variations, modifications, and embodiments are possible, and accordingly, all such variations, modifications, and embodiments are to be regarded as being within the spirit and scope of the invention.

The invention claimed is:

1. A method for increasing the acid tolerance of a *Lactobacillus reuteri* ATCC 55730 comprising removing a plasmid selected from the group consisting of pLR581 and pLR585 from *Lactobacillus reuteri* ATCC 55730 and recovering the strain produced.

\* \* \* \* \*

UNITED STATES PATENT AND TRADEMARK OFFICE
CERTIFICATE OF CORRECTION

PATENT NO.        : 8,603,460 B2                                    Page 1 of 1
APPLICATION NO.   : 11/446648
DATED             : December 10, 2013
INVENTOR(S)       : Eamonn Connolly It is certified that error appears in the above-identified patent and that said Letters Patent is hereby corrected as shown below:

On the title page, item (73) should be corrected to read: Assignee: Biogaia AB, Lerum (SE)

Signed and Sealed this
Twenty-seventh Day of May, 2014

Michelle K. Lee
*Deputy Director of the United States Patent and Trademark Office*